United States Patent [19]

Bauer

[11] Patent Number: 5,902,896

[45] Date of Patent: May 11, 1999

[54] PROCESS FOR PREPARING BIS (HYDROXYMETHYL) COMPOUNDS

[75] Inventor: Frank Bauer, Mobile, Ala.

[73] Assignee: Huels Aktiengesellschaft, Marl, Germany

[21] Appl. No.: 09/044,994

[22] Filed: Mar. 20, 1998

[30] Foreign Application Priority Data

Mar. 21, 1997 [DE] Germany ............................ 197 11 762

[51] Int. Cl.$^6$ .......................... C07C 255/00; C07C 69/00; C07C 249/00; C07C 49/213

[52] U.S. Cl. .......................... 558/451; 560/129; 564/192; 564/248; 568/308; 568/382; 568/420; 568/852

[58] Field of Search ............................ 558/451; 560/129; 564/192, 248; 568/308, 382, 420, 852

[56] References Cited

U.S. PATENT DOCUMENTS 5,132,006  7/1992  Neumann et al. .
5,254,757  10/1993  Merger et al. ............................ 568/852

*Primary Examiner*—Deborah C. Lambkin
*Assistant Examiner*—Joseph Murray

*Attorney, Agent, or Firm*—Oblon, Spivak, McClelland, Maier & Neustadt, P.C.

[57] ABSTRACT

A process for preparing bis(hydroxymethyl) compounds of the formula (I)

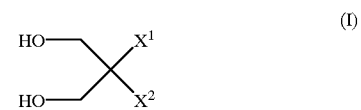

wherein $X^1$ and $X^2$ represent identical or different electronegative groups, which process entails reacting C—H-acidic compounds of the formula (II)

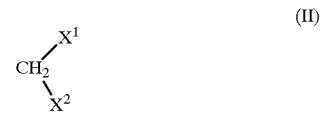

wherein $X^1$ and $X^2$ are as defined above, with formaldehyde, wherein the reaction is carried out in an anhydrous medium.

17 Claims, No Drawings

PROCESS FOR PREPARING BIS (HYDROXYMETHYL) COMPOUNDS

BACKGROUND OF THE INVENTION

1. Field of the Invention

The present invention relates to a process for preparing bis(hydroxymethyl) compounds.

2. Description of the Background

Bis(hydroxymethyl) compounds of the formula (I):

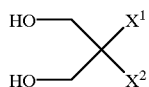
(I)

wherein $X^1$ and $X^2$ are the same or different electronegative groups, are presently used as intermediates in the preparation of UV stabilizers or radioopaque media. See, for example, EP-A2 0 220 034.

Current methods for preparing compounds of the formula I usually start from the corresponding C—H-acidic compounds of the formula (II):

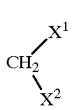
(II)

where $X^1$ and $X^2$ are as defined above. These compounds are reacted in aqueous reaction media in a Knoevenagel condensation.

If the reaction is carried out as described for the industrially important diethyl bis(hydroxymethyl) malonate (see (a) Gault, Rosesch; Bull. Soc. Chim. Fr. (5)4 (1937), 1411; and (b) Lenz, R. W.; Saunders, K.; Balakrishnan, T.; Macromolecules 12, 3 (1979), 392; and (c) Chang, H. M. et al.; J. Med. Chem. 34 (1991), 5, 1675) and ethyl bis (hydroxymethyl) cyanoacetate (see Tschierske, C.; bis (hydroxymethyl) cyanoacetate (see Tschierske, C.; Vorbrodt, H. -M.; Kresse, H., Zaschke, H.; Mol. Cryst. Liq. 177 (1989), 113), in aqueous solution using $KHCO_3$, $K_2CO_3$ or NaOH as a catalyst, the selectivities observed are indeed very good, compared with acid catalysis. Implementing the method on an industrial scale, however, entails a number of serious drawbacks, in particular relating to the removal of water and the isolation of the product.

Thus, as a rule, isolation by distillation is out of the question, due to considerable losses in product resulting from thermal decomposition. The gaseous decomposition products formed in the process (Welch, J., J. Chem. Soc. 1930 258), moreover, mean that a stable vacuum cannot be achieved. Isolating the bis(hydroxymethyl) compounds by extraction from the aqueous reaction solution is very laborious, particularly with the industrially important bis (hydroxymethyl) malonic esters where $R^1$, $R^2$=—$COOCH_3$ or —$COOC_2H_5$, as these are highly water-soluble.

While, the diethyl bis(hydroxymethyl) malonate can be extracted from the aqueous reaction solution by being salted out with ammonium chloride, according to *Organic Synthesis*, 40, 27, this results in the entire nitrogen load remaining in the aqueous phase, requiring complex disposal measures. Moreover, multistage extractions mean that not only the desired products, but also considerable amounts of water pass into the organic phase. This has adverse consequences particularly in those cases where further processing of the bis(hydroxymethyl) malonic esters must be carried out under anhydrous conditions.

Since the bis(hydroxymethyl) compounds of the formula (I) are all quite polar and, consequently, readily water-soluble and somewhat thermally unstable, similar problems are also encountered with the other bis(hydroxymethyl) compounds of this formula.

Irrespective of the type of method used for isolating the bis(hydroxymethyl) compounds of the formula (I), the preparation of these compounds yields wastewater streams which are not entirely free from formaldehyde and, thus, not readily disposable. This is virtually prohibitive for the preparation of bis(hydroxymethyl) compounds of the formula (I) on an industrial scale.

Moreover, the bis(hydroxymethyl) compounds of the formula (I), being typical organic intermediates, must often be used in anhydrous form, in order to achieve high yields or utilize simple procedures in subsequent reactions, e.g. the reaction to 2-substituted 1,3-dioxane-5,5-dicarboxylic acid derivatives in accordance with a currently pending German patent application.

Anhydrous processes have also been disclosed. For example, the preparation of diethyl bis(hydroxymethyl) malonate by reacting diethylmalonate with paraformaldehyde in acetic acid in the presence of copper acetate at comparatively high temperatures has been described (Japan. patent appl. 072564), where the laborious removal of water is, of course, avoided. However, O-acetylated and non-acetylated compounds are produced in a mixture which can only be separated with difficulty, and the selectivity for the desired non-acetylated compound is low (Kunichika, S.; Oka, S.; Sugiyama, T.; Nakamura, K.; Fukui, K.; Nippon Kagaku Kaishi 3 (1972), 596). Moreover, the use of reaction temperatures above 50° C., which are required for a satisfactory space-time yield, results in considerable product losses by thermal decomposition and by the formation of diethyl methylenemalonate.

It is also known that malonitrile can be reacted in glacial acetic acid, in the presence of potassium acetate, with gaseous formaldehyde at 100° C. to produce bis(methylol) malonitrile (Ardis, A. E.; Averill, S. J.; Gilbert, H.; Miller, F. F.; Schmidt, R. F.; Stewart, F. D.; and Trumbull, H. L.; J. Am. Chem. Soc., 72 (1950), 1305), although the yield is only 24% of the theoretical yield.

There, a need exists for a process for the bis-hydroxymethylation of compounds of the above formula (II), which affords high yields of the corresponding bis (hydroxymethyl) compounds of the above formula (I) which can be further reacted with high yields, either in the pure form or alternatively in a reaction mixture, and which process does not produce any wastewater containing salts, such as ammonium salts, for example, and/or formaldehyde.

SUMMARY OF THE INVENTION

Accordingly, it is the object of the present invention to provide a process for preparing bis(hydroxymethyl) compounds in high yield.

It is also an object of the present invention to provide a process for preparing bis(hydroxymethyl) compounds without producing any wastewater containing ammonium salts or other salts and/or formaldehyde.

The above objects and others are provided by a process for preparing bis(hydroxymethyl) compounds of the formula (I):

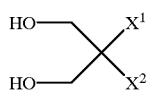

wherein $X^1$ and $X^2$ are each, independently of another, the same or different electronegative groups, which process entails reacting one or more C—H-acidic compounds of the formula (II):

wherein $X^1$ and $X^2$ are as defined above, with formaldehyde, wherein the reaction is effected in an anhydrous medium.

DETAILED DESCRIPTION OF THE PREFERRED EMBODIMENTS

Accordingly, the present invention is predicated upon the surprising discovery that bis(hydroxymethyl) compounds of the formula (I):

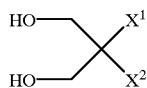

wherein $X^1$ and $X^2$ represent identical or different electronegative groups may be advantageously obtained by reacting —C—H-acidic compounds of the formula (II):

wherein $X^1$ and $X^2$ are as defined above, with formaldehyde by carrying out the reaction in an anhydrous medium.

In the preferred bis(hydroxymethyl) compounds of the formula (I) and C—H-acidic compounds of the formula (II), $X^1$ and $X^2$, independently of one another, represent the groups —COOR, —CONR$_2$, —CN, —NO$_2$, —C(OR)=NR or —COR, R being hydrogen, alkyl, aralkyl, aryl or cycloalkyl each having up to about 12 carbon atoms, with the proviso that (i) the two substituents $X^1$ and $X^2$ cannot simultaneously represent —COOH, and (ii), if the two substituents $X^1$ and $X^2$ simultaneously represent —CO—R, the two substituents R together may also represent an alkylene radical having from 2 to about 9 carbon atoms.

In the particularly preferred bis(hydroxymethyl) compounds of the formula (I) and C—H-acidic compounds of the formula (II), $X^1$ and $X^2$, independently of one another, are —COOR or —CN, and R is a $C_1$-$C_4$-alkyl radical.

Examples of suitable C—H-acidic compounds of the formula (II) are dimethyl malonate, diethyl malonate, di-n-propyl malonate, diisobutyl malonate, dibenzyl malonate, 2-ethylhexyl malonate, ethyl - N-N-dimethylcarbamidoacetate, N,N,N', N'-tetramethylmalonamide, malonitrile, ethyl cyanoacetate, n-butyl cyanoacetate, ethyl nitroacetate, acetylacetone and cyclododeca-1,3-dione, for example.

Formaldehyde can be employed as a gaseous product, but is preferably used in the form of solid paraformaldehyde. The C—H-acidic compound of the formula (II) and the formaldehyde can be used in stoichiometric amounts, i.e. in a molar ration of about 2:1, although a slight excess of one or the other component, in particular formaldehyde, is acceptable.

The present process is advantageously carried out in the presence of a basic catalyst. Suitable as such are, in particular, metal hydroxides, metal carbonates, metal hydrogen carbonates, basic ion exchangers or alcoholates. Preference is given to alkali metal hydroxides, alkali metal carbonates, alkali metal hydrogen carbonates and alkali metal alcoholates and to basic ion exchangers carrying quaternary ammonium groups. The catalyst may be solid (i.e. suspended in the reaction mixture of fixed as a supported catalyst) or dissolved in the reaction mixture. Particularly suitable as dissolved catalysts are the alkali metal alcoholates, particularly, as explained below, if an alkanol is used concomitantly as a solvent. They are expediently employed in amounts from about 0.01 to 5.0 wt %, in particular from about 0.01 to 2.0 wt %, based on the C—H-acidic compound of the formula (II). Suitable solid catalysts, suspended in the reaction mixture or possible partly dissolved therein are, inter alia, potassium hydrogen carbonate, potassium carbonate, sodium carbonate and sodium hydrogen carbonate. The amount of these is expediently from about 0.01 to 10 wt %, based on the C—H-acidic compound of the formula (II). If acidic ion exhangers are used, the amount of these can be considerably higher. This is the case e.g. if the starting mixture is made to flow across fixed acidic ion exchangers.

The use of a solvent is not strictly necessary, but use of a solvent simplifies control of the reaction and handling of the reaction mixture. In principle, any solvent may be used which does not react with the starting materials of the formula (II) and formaldehyde under the reaction conditions chosen. In practice, however, particularly in those cases where formaldehyde is employed as paraformaldehyde, the use of polar solvents, in particular of alkanols, is advantageous. Solvent mixtures may also be used, of course, however, it is generally less favorable to use acidic solvents, such as acetic acid. The proportion of the solvent or solvent mixture in the reaction mixture is generally from about 10 to 80.0% by weight at the end of the reaction. Of course, the reaction can also be carried out at even greater dilution with solvent, but the space-time yield is reduced.

The present process affords the important advantage that the reaction can be carried out in an anhydrous medium. As already mentioned, wastewater problems and the difficulties of obtaining the product from aqueous mixtures are, thereby, avoided. Considerable advantages compared with the processes in an aqueous medium are also obtained, however, if the reaction mixture is only substantially anhydrous, i.e. contains only small amounts of water, e.g. up to about 5.0% by weight. Such small amounts may, inter alia, be carried by the solvent. The reaction under such substantially anhydrous conditions explicitly falls within the scope of the present invention.

The present process is carried out at reaction temperatures of from about –30° C. to 200° C., the reaction times being tailored to the reaction temperatures in such a way that appreciable decomposition of the bis(hydroxymethyl) compounds of the formula (I) is virtually precluded. For batch-type embodiments of the present process, the reaction rates at which the bishydroxymethylation proceeds at temperatures below –30° C. are generally too slow, whereas, not infrequently, strong decomposition reactions occur above 120° C. Sufficiently rapid reactions and high selectivities are achieved in the temperatures range of from about 0° C. to 60° C. and, in particular, in the temperature range of from about 15° C. to 30° C. Accordingly, these temperature ranges are particularly preferred. Particularly, if formaldehyde is employed as paraformaldehyde, the temperature increase towards the end of the reaction favors high space-time yields and high conversion ratios. The reaction times in the batch-type version of the process are generally from about 0.5 to 5.0 hours.

For continuous preparation of the bis(hydroxymethyl) compounds of the formula (I), temperatures up to 200° C. and higher are possible, while at the same time the reaction times are shortened, sometimes drastically. Suitable combinations of reaction temperature and reaction time can readily be found, for a given reaction system, by facsimile preliminary experiments which are well within the skill of the artisan in view of this disclosure.

An advantageous embodiment quite useful in practice entails the addition of the C—H-acidic compound of the formula (II) to a suspension of paraformaldehyde in an inert solvent or solvent mixture or to a solution of formaldehyde in an inert solvent or solvent mixture. In addition to comparatively high selectivities this procedure ensures that the liberated heat of reaction can be removed safely. In many cases the product can be processed further without catalyst separation. Of course, the catalyst may also be separated off, e.g. by filtration, if the catalyst is a solid, or by neutralization with an acid and removal by filtration of the salt formed, if a dissolved catalyst had been used. In the latter case, expediently, an essentially nonpolar solvent is added in which, however, the bis(hydroxymethyl) compounds of the formula (I) are soluble, since the latter are generally polar solids. Examples of suitable, comparatively nonpolar solvents are diisopropyl ether, methyl t-butyl either and ethyl acetate, for example. After the possibly neutralized catalyst has been separated off, the solvent can be removed, under reduced pressure if required, and the residue obtained is the bis(hydroxymethyl) compound of the formula (I).

The bis(hydroxymethyl) compounds of the formula (I), obtained according to the present process in anhydrous or substantially anhydrous form, can be used directly as such, after removal of the solvent, or in the form of the reaction mixture which has not been worked up, or in further syntheses which require an anhydrous or virtually anhydrous starting material. It is a particular advantage of the present process that the bis(hydroxymethyl) compounds of the formula (I) can be further reacted in the reaction mixture in which they are produced, without isolation or purification, to afford yields of subsequent product, which are almost as good as would result from the use of isolated bis (hydroxymethyl) compounds of the formula (I).

Having described the present invention, reference will now be made to certain examples which are provided solely for purposes of illustration and which are not intended to be limitative.

EXAMPLE 1

Diethyl bis(hydroxymethyl) malonate

Over a period of 1.75 hours, 160.2 g of diethyl malonate (1.0 mol) were added to a suspension, stirred at from 25° C. to 30° C., of 60.0 g of paraformaldehyde (2.0 mol) and 0.25 g of sodium ethylate in 40.0 g of ethanol. After a post-reaction time of 2 hours at 50° C. the mixture was cooled to 45° C. and 0.36 g of concentrated sulfuric acid were added. After cooling to room temperature, the precipitated white solid was filtered off with suction through a glass filter nutsche. The colorless filtrate obtained was freed from low-boiling compounds in a water jet vacuum (16 mm) at a bath temperature of 60° C., 121.2 g (96% of the theoretical yield according to final weight) of reaction product remaining in the form of a clear, colorless oil. The purity of the material, determined by gas chromatography, was found to be 85 FID % by area after silylation.

EXAMPLE 2

Ethyl bis(hydroxymethyl) cyanoacetate

Over a period of 2.0 hours, 113.0 g of ethyl cyanoacetate (1.0 mol) were added to a mixture, stirred at from 0° C. to 10° C., of 62.0 g of paraformaldehyde (2.1 mol), 200 g of ethanol and 0.25 g of sodium ethylate. The reaction mixture was then stirred at 10° C. for 1 hour longer, before being warmed to room temperature over a period of 10 minutes.

The colorless clear solution thus obtained was freed from solvent on a rotary evaporator at an 8 mbar vacuum, 175.1 g of ethyl bis(hydroxymethyl) cyanoacetate being obtained which had a purity, determined by gas chromatography, of 71.2 FID % by area (silylated sample). Taking the product purity into account, the yield was 72.9% of the theoretical yield, based on ethyl cyanoacetate used.

Having further described the present invention, it will now be apparent to one of ordinary skill in the art that many changes and modifications may be made to the above-described embodiments without departing from the spirit and the scope of the present invention.

What is claimed as new and is desired to be secured by Letters Patent of the United States is:

1. A process for preparing bis(hydroxymethyl)compounds of the formula (I):

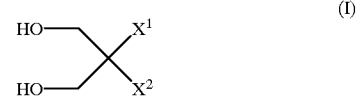

where $X^1$ and $X^2$ represent identical or different electronegative groups selected from the group consisting of —COOR, —CONR$_2$, —CN, —NO$_2$, —C(OR)=NR and —COR, where R is hydrogen, alkyl, aralkyl, aryl or cycloalkyl each having up to about 12 carbon atoms, with the proviso that (i) where the two substituents $X^1$ and $X^2$ simultaneously represent —CO—R', the two substituents R' together may also represent an alkylene radical having from 2 to 9 carbon atoms, which process entails reacting C—H-acidic compounds of the formula (II) with paraformaldehyde,

wherein the reaction is effected in a substantially anhydrous medium with a basic catalyst selected from the group consisting of a metal hydroxide, metal carbonate, metal hydrogen carbonate, basic ion exchange, or an alcoholate.

2. The process of claim 1, wherein $X^1$ and $X^2$, independently of one another, are —COOR or —CN, where R is a $C_1$–$C_4$-alkyl radical.

3. The process of claim 1, wherein the formaldehyde is employed in the form of paraformaldehyde.

4. The process of claim 1, wherein a polar solvent is used concomitantly.

5. The process of claim 4, wherein the polar solvent is a $C_1$–$C_4$-alkanol.

6. The process of claim 1, wherein the basic catalyst is an alkali metal hydroxide, alkali metal carbonate, alkali metal hydrogen carbonate or an alcoholate.

7. The process of claim 1, which is carried out batchwise at a reaction temperature is from about −30° C. to 120° C.

8. The process of claim 7, which is carried out batchwise at a reaction temperature of from about 0° C. to 60° C.

9. The process of claim 7, which is carried out continuously at a reaction temperature of up to about 200° C.

10. The process of claim 1, which is carried out batchwise with the C—H-acidic compound of the formula (II) being added to a suspension of paraformaldehyde in a solvent or solvent mixture.

11. The process of claim 1, wherein, after the reaction is complete, the solid catalyst is separated off or the dissolved catalyst is neutralized and the salt formed in separated off.

12. The process of claim 1, wherein the bis (hydroxymethyl) compound of the formula (I) is further reacted in the reaction mixture in which it is formed, without being isolated.

13. The process of claim 1, wherein said C—H acidic compounds of the formula (II) are selected from the group consisting of dimethyl malonate, diethyl malonate, di-n-propyl malonate, diisobutyl malonate, dibenzyl malonate, 2-ethylhexyl malonate, ethyl-N,N-dimethylcarbamidoacetate, N,N,N',N'-tetramethylmalonimide, malonitrile, ethyl cyanoacetate, n-butyl cyanoacetate, ethyl nitroacetate, acetylacetone and cyclododeca-1,3-dione.

14. The process of claim 1, wherein said basic catalyst is a dissolved catalyst and is used in an amount of about 0.01 to 5.0 wt. % based on the amount of C—H acidic compound used.

15. The process of claim 1, wherein said basic catalyst is a solid or partialy dissolved catalyst and is used in an amount of about 0.01 to 10.0 wt. % based on the amount of C—H acidic compound used.

16. The process of claim 10, where said paraformaldhyde is in a suspension of alkanol.

17. The process of claim 1, wherein said compound of the formula (I) is selected from the group consisting of diethyl bis(hydroxymethyl)malonate and ethyl bis(hydroxymethyl) cyanoacetate.

* * * * *